United States Patent [19]
Nakano et al.

[11] Patent Number: 5,185,082
[45] Date of Patent: Feb. 9, 1993

[54] METHOD FOR EVALUATING THE VIRUS-REMOVING CAPABILITY OF A POROUS POLYMERIC MEMBRANE MODULE FOR REMOVING VIRUSES

[75] Inventors: Hiroo Nakano, Nobeoka; Seiichi Manabe, Kyoto, both of Japan

[73] Assignee: Asahi Kasei Kogyo Kabushiki Kaisha, Osaka, Japan

[21] Appl. No.: 894,544

[22] Filed: Jun. 5, 1992

[30] Foreign Application Priority Data

Jun. 6, 1991 [JP] Japan .................................. 3-135069

[51] Int. Cl.$^5$ .............................................. B01D 63/02
[52] U.S. Cl. ....................................... 210/639; 73/861
[58] Field of Search ............... 210/634, 637, 639, 645; 73/23.2, 861, 861.04, 861.06, 861.05

[56] References Cited

U.S. PATENT DOCUMENTS 4,808,315  3/1989  Manabe et al. ..................... 210/645

Primary Examiner—Frank Sever
Attorney, Agent, or Firm—Finnegan, Henderson, Farabow, Garrett, Dunner

[57] ABSTRACT

Disclosed is a method for the evaluation of the virus-removing capability of a porous polymeric membrane module for removing viruses by filtration, which comprises testing I in which a transmembrane pressure lowering from predetermined value Ph a predetermined period of time after the termination of the supply of a gas is measured with respect to the porous polymeric membrane module, wherein the value Ph satisfies the formula: d<Ph<c, wherein d and c are respectively the transmembrane pressures at points (d) and (c) in FIG. 1 hereof. By the method of the present invention, it has become possible for the first time to effectively and efficiency select a module which can be suitably used for removing viruses from a virus-containing fluid and to obtain to fluid substantially free of the virus.

9 Claims, 3 Drawing Sheets

FIG.3

Φ for JEV (y-axis, values 0, 3, 4.5, 6)

Transmembrane pressure lowering (atm) (x-axis, values 0, 2, 2.5, 4, 6, 8, 10)

METHOD FOR EVALUATING THE VIRUS-REMOVING CAPABILITY OF A POROUS POLYMERIC MEMBRANE MODULE FOR REMOVING VIRUSES

BACKGROUND OF THE INVENTION

1. Field Of The Invention

The present invention relates to a method for evaluating the virus-removing capability of a porous polymeric membrane module for removing viruses by filtration. More particularly, the present invention is concerned with a method for evaluating the virus removing capability of a porous polymeric membrane module for removing viruses by filtration from a virus-containing fluid, which method comprises filling a space on one side of the membrane of the module with a liquid, supplying another space on the other side of the membrane with a gas, terminating the supply of the gas when the transmembrane pressure on the membrane reaches a predetermined level (higher than a level at which non-visible bubbles begin to form but lower than level at which visible bubbles begin to form), allowing the module to stand to thereby cause the transmembrane pressure to be lowered, and measuring the transmembrane pressure lowering a predetermined period of time after the termination of the supply of the gas. By the method of the present invention, the capability of a module to remove viruses can be effectively and efficiently evaluated, thereby enabling the selection of a module which has at least a predetermined level of virus-removing capability and which can be suitably used for removing viruses from a fluid which may contain a virus, for example, protein solutions, such as a plasma, a plasma fractionation product, a culture medium used for cell culturing, and biological pharmaceutical products.

2. Discussion Of Related Art

In recent years, separation techniques using a polymeric membrane have made marked progress and have been used in a wide variety of application fields. The separation techniques using a polymeric membrane are classified into two types according to the principal mechanism of separation, that is, separation by filtration based on the difference between the pore diameter of a porous membrane and the size of a substance to be removed, and separation based on various physical and chemical interactions, such as an adsorption etc., between a membrane and a substance to be removed.

In removing viruses from a virus-containing fluid, however, a porous polymeric membrane module employing the former type of separation technique (filtration) is especially advantageously employed.

With respect to the separation technique for removing viruses from a virus-containing fluid by filtration using a porous polymeric membrane module, various proposals have been made. Examples of such separation techniques are disclosed in Japanese Patent Application Laid-Open Specification Nos. 60-142860, 60-142861 and 61-168367 (in each of which a porous polyolefin membrane is used); U.S. Pat. Nos. 4,808,315 and 4,857,196 and Japanese- Patent Application Laid-Open Specification Nos. 61-254202 and 61-274707 (in each of which a porous regenerated cellulose membrane is used); and Japanese Patent Application Laid-Open Specification No. 62-266072 (in which a porous substance comprising calcium phosphate as a main component, is used).

Meanwhile, since the virus-removing capability of a porous polymeric membrane module is largely influenced by the pore diameter of the membrane, the selection of a porous polymeric membrane module having a predetermined virus-removing capability, has conventionally been conducted mainly by the measurement of the pore diameter of the membrane. Thus, many methods for measuring the pore diameter of a porous membrane have conventionally been known. However, as will be described below in detail, none of the conventional methods are satisfactory as a method for measuring the virus-removing capability of a porous polymeric membrane module for removing viruses.

For example, the mercury intrusion method is known. However, in the mercury intrusion method, the measurement of the pore diameter of a porous polymeric membrane (the diameter is of a submicron order) requires application of an extremely high pressure to a porous polymeric membrane, so that the porous membrane is likely to be damaged. Therefore, this method is unsuitable for the measurement of the pore diameter of a porous polymeric membrane module for removing viruses.

Further, the so-called bubble point test is known in which a first space on one side of a porous polymeric membrane of a module is filled with water and a second space on the other side of the membrane is supplied with a gas and the transmembrane pressure at the time when clear formation of visually observable bubbles occurs, is measured. However, in the case of a porous polymeric membrane having a pore diameter of 100 nm (=0.1 $\mu$m) or less, such as membranes for use in removing viruses, the measurement of the pore diameter by the bubble point test requires application of a pressure as high as 30 kg/cm$^2$ or more, so that the membrane is likely to be damaged. Therefore, this method is unsuitable for the selection of a porous polymeric membrane module for removing viruses.

There is also known a method in which the measurement of the pore diameter is conducted by observing pores through an electron microscope. This method has an advantage in that the pore diameter of individual pores can be directly and accurately measured. However, this method has the following serious disadvantages. That is, the greater the magnification of the electron microscope, the more the area of a portion which can be observed is limited. In general, for obviating this disadvantage, it is necessary that electro photomicrographs of numerous portions of the membrane be taken, thus causing the procedure to be extremely cumbersome. Further, it is impossible to measure the diameters of all of the vast plurality of pores of a membrane, so that measurement of pore diameters cannot be conducted with respect to the entire membrane. Therefore, this method cannot be practically used.

As a relatively practical method, a method is known in which the rate of permeation of water through a porous membrane is measured, to thereby determine the average pore diameter of the membrane. However, with this method, it is impossible to measure a distribution of pore diameters of the membrane, so that the ratio of pores having a pore diameter larger than the average pore diameter and the magnitude of the difference from the average pore diameter (both of which have a great influence on the performance of a membrane) cannot be determined. Therefore, this method cannot be satisfactorily used for the selection of a porous polymeric membrane module for removing viruses.

In the field of filters for removing bacteria, several testing methods called "integrity tests" have been developed and used as methods for examining the capability of a filter to remove bacteria.

Among the integrity tests are a method in which a bubble point is measured as described above, and a diffusion method in which the degree of diffusion of a gas into a liquid through a membrane at a transmembrane pressure at which no bubbles are generated, is measured. The diffusion method can be further classified into a forward flow test in which the flow rate of a gas through a membrane while supplying the gas is measured, and a pressure hold test in which the gas supply is terminated at an appropriate transmembrane pressure and then, a transmembrane pressure lowering is measured a predetermined period after the termination of the supply of the gas (see, for example, "Field experience in testing membrane filter integrity by the forward flow test method", by Wayne Pauli, Ph. D., published by Pall Corporation, Glen Cove, N.Y., U.S.A.). Thus, these integrity tests can be roughly classified into two types of methods, that is, a method (bubble point test) in which a transmembrane pressure at which visually observable bubbles are generated, is measured, and a method (diffusion test) in which the degree of diffusion of a gas into a liquid through a membrane at a transmembrane pressure at which no bubbles are generated, is measured. Practically, the most suitable measuring method is selected, taking into consideration various factors, such as the porous structure, uniformity, strength and production method of the membrane to be examined.

In each of the above-mentioned integrity test methods for examining the capability to remove bacteria, water is mainly used as a liquid. In general, water is suitable as a liquid for use in testing a filter for removing bacteria, which filter has a maximum pore diameter as large as 0.5 μm or more. However, since water has a high surface tension, when water is used as a liquid in the measurement of the virus-removing capability of a module for removing viruses (in such a module the maximum pore diameter of the membrane is as small as 0.25 μm or less), the transmembrane pressure at which the measurement is conducted is inevitably too high, thus damaging the membrane contained in the module. Therefore, the above-mentioned integrity tests for bacteria-removing filters cannot be used for evaluating the virus-removing capability of a porous polymeric membrane module for removing viruses.

Thus, there have been no conventional testing methods which can be effectively and efficiently applied to the evaluation of the virus-removing capability of a porous polymeric membrane module for removing viruses without the danger of damaging the porous polymeric membrane.

In these situations, a novel method for evaluating the virus-removing capability of a porous polymeric membrane module for removing viruses has been earnestly desired.

SUMMARY OF THE INVENTION

With a view toward developing an effective and efficient method for the evaluation of the virus-removing capability of a porous polymeric membrane for removing viruses, the present inventors have made extensive and intensive studies. As a result, it has unexpectedly been found that this goal can be attained by a special pressure hold method in which the supply of a gas is terminated when a transmembrane pressure reaches predetermined value Ph satisfying the following formula:

$$d < Ph < c$$

wherein d and c are respectively the specific transmembrane pressures at points (d) and (c) in FIG. 1 hereof, and then, a transmembrane pressure lowering from value Ph a predetermined period of time after the termination of the supply of the gas is measured. The present invention is based on this novel finding.

It is, therefore, an object of the present invention to provide a method for the evaluation of the virus-removing capability of a porous polymeric membrane module for removing viruses, which method is free from the drawbacks of the conventional testing methods and can be performed at a relatively low transmembrane pressure, so that the selection of a porous polymeric membrane module for removing viruses, which module has a predetermined level of virus-removing capability, can be effectively and efficiently performed with high reliability and without the danger of damaging the membrane.

The foregoing and other objects, features and advantages have been achieved according to the present invention and will be apparent to those skilled in the art from the following detailed description and appended claims taken in connection with the accompanying drawings.

BRIEF DESCRIPTION OF THE DRAWINGS

In the drawings:

FIG. 3 is a graph showing the relationship between the transmembrane pressure lowering from value Ph a predetermined period of time after the termination of the supply of a gas in testing I and the capability to remove JEV (Japanese encephalitis virus) (JEV removal ratio) in terms of the logarithmic virus rejection coefficient (Φ) for JEV, which relationship is obtained with respect to a porous polymeric membrane module containing a porous polymeric membrane having an average pore diameter of 35±2.0 nm and a maximum pore diameter of about 60 nm to about 80 nm and having an effective surface area of 0.03 m².

DETAILED DESCRIPTION OF THE INVENTION

Figure 1:
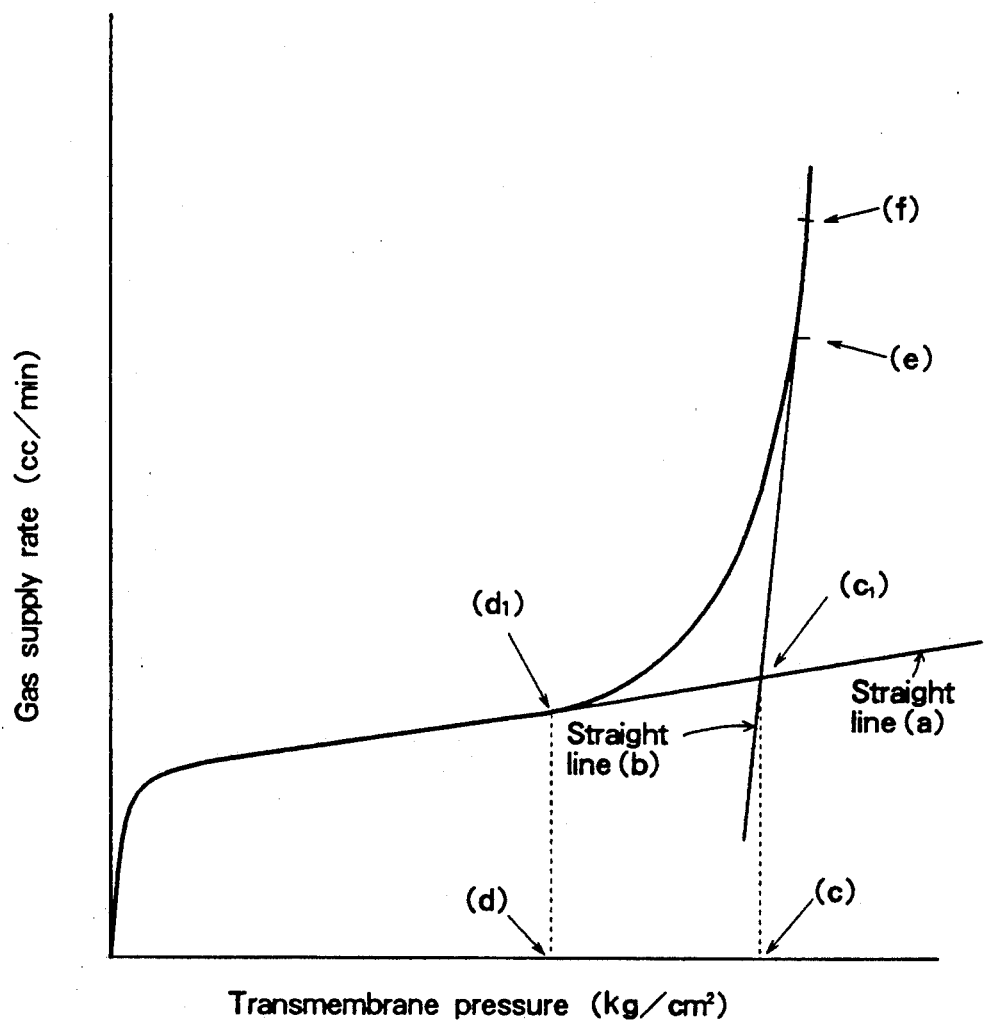
FIG. 1 is one example of a graph containing a curve showing the relationship between the transmembrane pressure and the gas supply rate of a model porous polymeric membrane module, in which graph points (d) and (c) are identified for determining value Ph which is essential to the present invention.

Essentially, according to the present invention, there is provided a method for evaluating the virus-removing capability of a porous polymeric membrane module for removing viruses from a virus-containing fluid by filtration, the module comprising a casing having an inlet for a virus-containing fluid and an outlet for a filtrate, and a porous polymeric membrane disposed in the casing to partition the interior of the casing into a first space on one side of the membrane which first space communicates with one of the inlet or the outlet and a second space on the other side of the membrane which second space communicates with the remaining one of the inlet or outlet, which method comprises subjecting the porous polymeric membrane module to testing I, the testing I comprising the steps of:

(1) filling the first space on one side of the membrane with a liquid, chemically inert to the membrane, (2) supplying the second space on the other side of the membrane with a gas, chemically inert to the membrane, (3) terminating the supply of the gas when the transmembrane pressure on the membrane reaches predetermined value Ph, the value Ph satisfying the following formula:

$$d < Ph < c$$

wherein d and c are respectively the transmembrane pressures at points (d) and (c) in FIG. 1 hereof, (4) allowing the module to stand, thereby causing the transmembrane pressure on the membrane to be lowered, and (5) measuring the transmembrane pressure lowering from value Ph a predetermined period of time after the termination of the supply of the gas, wherein FIG. 1 is a graph containing a curve showing the relationship between the transmembrane pressure and the gas supply rate of a model porous polymeric membrane module, said model module being substantially the same as said module to be subjected to testing I, containing a porous polymeric membrane having an average pore diameter and a maximum pore diameter which are, respectively, within ranges which are predetermined in accordance with the size of viruses to be removed, the relationship between the transmembrane pressure and the gas supply rate being obtained by filling the first space on one side of the membrane of the model module with a liquid chemically inert to the membrane and supplying the second space on the other side of the membrane of the model module with a gas chemically inert to the membrane while measuring the transmembrane pressure and the gas supply rate, and wherein:

a straight line obtained by extending the straight line portion first occurring in the curve of FIG. 1 is defined as straight line (a), the first occurring straight line portion of the curve representing the increase in gas supply rate in proportion to the increase in transmembrane pressure, a transmembrane pressure at point (d) corresponding to point ($d_1$) on the curve at which point ($d_1$) the curve starts to diverge from the straight line (a), is defined as transmembrane pressure d, a straight line obtained by connecting points (e) and (f) on the curve at which points (e) and (f) the gas supply rates are, respectively, 2.5 times and 3.0 times the gas supply rate at point ($d_1$), is defined as straight line (b), and a transmembrane pressure at point (c) corresponding to point ($c_1$) at which straight line (a) intersects with straight line (b), is defined as transmembrane pressure c.

In the method of the present invention, the porous polymeric membrane module to be subjected to testing I comprises a casing having an inlet for a virus-containing fluid and an outlet for a filtrate, and a porous polymeric membrane disposed in the casing. The porous polymeric membrane partitions the interior of the casing into a first space on one side of the membrane which first space communicates with one of the inlet or the outlet and a second space on the other side of the membrane which second space communicates with the remaining one of the inlet or outlet.

With respect to the type of the porous polymeric membrane contained in the module, there is no particular limitation as long as it has a porous structure suitable for removing viruses. Examples of such membranes include various types of membranes, such as a hollow fiber membrane, a plane membrane, and a tube-shaped membrane having an outer diameter which is greater than that of a hollow fiber membrane. Of these membranes, from the viewpoint of attaining a large effective surface area per unit volume of the module, a hollow fiber membrane is preferred.

With respect to the type of the module, there is no particular limitation. Examples of types of modules include various types, such as a stacked layer type, a pleated type, and an artificial kidney type in which both ends of a bundle of a plurality of hollow fiber membranes are fixed by a potting resin or the like. Among these modules, modules containing porous polymeric membranes of the type disclosed in U.S. Pat. Nos. 4,808,315 and 4,857,196 can be advantageously used.

With respect to the material for a porous polymeric membrane, there is no particular limitation. That is, the material for a porous polymeric membrane may be either an organic polymer or an inorganic polymer. Examples of such materials include organic polymers, such as synthetic polymers, e.g., a polyolefin, nylon and polyester; cellulose derivatives; regenerated celluloses, such as a cuprammonium cellulose, viscose rayon and acetylated cellulose, which are obtained by subjecting cellulose derivatives to such treatment as saponification; a naturally occurring polymer; and inorganic polymers, such as glass and ceramic types. Of these, cuprammonium regenerated cellulose is most preferred because it has excellent permeability for protein and has actually been widely used in artificial kidneys and the like.

The method of the present invention comprises subjecting the porous polymeric membrane module to testing I described below. By testing I, the virus-removing capability of a porous polymeric membrane module can be evaluated.

Testing I of the method of the present invention comprises the following steps:

(1) filling the first space on one side of the membrane with a liquid, chemically inert to the membrane, (2) supplying the second space on the other side of the membrane with a gas, chemically inert to the membrane while increasing the supply rate of the gas, (3) terminating the supply of the gas when the transmembrane pressure on the membrane reaches predetermined value Ph, the value Ph satisfying the following formula:

$$d < Ph < c$$

wherein d and c are respectively the transmembrane pressures at points (d) and (c) in FIG. 1 hereof, (4) allowing the module to stand, thereby causing the transmembrane pressure on the membrane to be lowered, and (5) measuring the transmembrane pressure lowering from value Ph a predetermined period of time after the termination of the supply of the gas.

Following the above-mentioned testing I, selection of a module having at least a predetermined level of virus-removing capability can be done by a method comprising the steps of:

(6) determining whether the measured transmembrane pressure lowering is not greater than a value which is predetermined in accordance with a preselected virus removal ratio, and (7) identifying the module as qualified or disqualified, based on said determination in step (6).

As mentioned above, FIG. 1 is a graph containing a curve showing the relationship between the transmembrane pressure and the gas supply rate of a model polymeric membrane module, the model module being substantially the same as the module to be subjected to testing I, containing a porous polymeric membrane having an average pore diameter and a maximum pore diameter which are, respectively, within ranges which are predetermined in accordance with the size of viruses to be removed.

With respect to an example of the actual procedure for preparation of FIG. 1, explanation is made below in detail.

The procedure comprises, for example;

(1) a desired average pore diameter for porous polymeric membranes of modules to be produced (and to be evaluated by the method of the present invention) is specified and then, conditions for producing porous polymeric membranes having the above-specified average pore diameter are established;

(2) with respect to porous polymeric membranes to be produced in accordance with the established production conditions, acceptable ranges respectively for the average pore diameter and the maximum pore diameter (obtained from the bubble point pressure described below) are determined;

(3) using the porous polymeric membranes produced under the above-mentioned production conditions and identified as qualified in accordance with the above-determined acceptable ranges of the average pore diameter and the maximum pore diameter, model modules are constructed;

(4) on the other hand, types of liquid and gas to be used in the method of the present invention are specified; and (5) the relationship between the transmembrane pressure and the gas supply rate of the model porous polymeric membrane module constructed in item (3) above is obtained by filling a first space on one side of the membrane of the model module with the liquid specified in item (4) above and supplying a second space on the other side of the membrane of the model module with the gas specified in item (4) above to the membrane while measuring the transmembrane pressure and the gas supply rate, and a graph as shown in FIG. 1 is prepared and transmembrane pressure values at points (d) and (c) (which are defined below) are obtained, wherein graphs are respectively prepared with respect to at least three model modules constructed in item (3) above, and (a) transmembrane pressures at points (d) and (c) are obtained with respect to all of the at least three model modules, and the obtained transmembrane pressure values at each of points (d) and (c) are averaged, or (b) an average graph is selected from the at least three graphs, and transmembrane pressure values at points (d) and (c) are obtained with respect to the selected average graph.

In connection with the preparation of FIG. 1, particularly with items (1), (2), (3) and (5) above, it should be noted that the porous polymeric membrane module to be evaluated with respect to a virus-removing capability thereof by the method of the present invention is specified depending on the type of a virus to be removed from a virus-containing fluid. The size of a virus depends on the type of the virus. For example, Japanese encephalitis virus has a size of about 45 nm and AIDS virus has a size of about 100 nm. That is, it is necessary that the average pore diameter and the maximum pore diameter of the porous polymeric membrane of the model module fall within respective ranges which are predetermined in accordance with the size of a virus to be removed. Accordingly, in item (2) above, the acceptable ranges for the average pore diameter and the maximum pore diameter of the membrane of each of the at least three model modules to be used for obtaining the transmembrane pressure-gas supply rate relationship represented by FIG. 1, are determined, based on the desired average pore diameter which is specified in item (1) above in accordance with the size of a virus to be removed. The range for the average pore diameter is defined by $\overline{D} \pm 0.1 \times \overline{D}$ wherein $\overline{D}$ represents the desired average pore diameter specified in item (1) above and the range for the maximum diameter is from $1.5\overline{D}$ to $5\overline{D}$ wherein $\overline{D}$ is as defined above.

In item (3) above, the average pore diameters and the maximum pore diameters of the membranes of the constructed model modules are measured.

The average pore diameter of a porous polymeric membrane can be determined by calculation from the water permeability according to the following formula:

$$2r_f = 2.0 \sqrt{\frac{v \times t \times \mu}{\Delta P \times A \times \alpha}}$$

wherein $2r_f$ is the average pore diameter, v is the water permeability (ml/min), t is the wall thickness (μm) of the membrane, $\mu$ is the viscosity of water (cp), $\Delta P$ is the transmembrane pressure (mmHg) at which the water permeability is measured, A is the effective surface area (m²) of the membrane and $\alpha$ is the porosity (%) of the membrane.

Alternatively, measurement of an average pore diameter may be conducted by other conventional methods. For example, a method in which a pore diameter is directly measured through an electron microscope may be employed.

The maximum pore diameter of a porous polymeric membrane can be determined, for example, by calculation using the bubble point pressure (transmembrane pressure at which visually observable bubbles begin to form) obtained by a bubble point test. A bubble point test can be conducted according to ASTM-F316-80. From the obtained bubble point value, a maximum pore diameter can be determined by calculation according to the following formula:

$$2r_{max} = \frac{4 \times \tau \times \cos\theta \times 100}{P \times 9.806}$$

wherein $2r_{max}$ is the maximum pore diameter, $\tau$ is the surface tension (dyne/cm) of the liquid used in the bubble point test, $\theta$ is the contact angle of the liquid used in the bubble point test and P is the transmembrane pressure (kg/cm²) corresponding to the bubble point.

Alternatively, measurement of a maximum pore diameter may be conducted by other conventional methods.

In FIG. 1, a straight line obtained by extending the straight line portion first occurring in the curve of FIG. 1 is defined as straight line (a). The first occurring straight line portion of the curve represents the increase in gas supply rate in proportion to the increase in transmembrane pressure. A transmembrane pressure at point (d) corresponding to point ($d_1$) on the curve at which point ($d_1$) the curve starts to diverge from the straight line (a), is defined as transmembrane pressure d. A straight line obtained by connecting points (e) and (f) on the curve, at which points (e) and (f) the gas supply rates are, respectively, 2.5 times and 3.0 times the gas supply rate at point ($d_1$), is defined as straight line (b) A transmembrane pressure at point (c) corresponding to point ($c_1$) at which straight line (a) intersects with straight line (b), is defined as transmembrane pressure c.

Straight line (a) in FIG. 1 obtained by extending the straight line portion first occurring in the curve represents the relationship between the transmembrane pressure and the gas supply rate during the diffusion of the gas from the gas-liquid interface into the liquid without generation of any bubbles.

Straight line (b) obtained by connecting points (e) and (f) on the curve, at which points (e) and (f) the gas supply rates are, respectively, 2.5 times and 3.0 times the gas supply rate at point ($d_1$), is derived from a portion of the curve corresponding to the generation of visually observable bubbles and has a correlation to the average pore diameter distribution of the at least three model modules.

The transmembrane pressure (c) corresponds to point ($c_1$) at which straight line (a) intersects with straight line (b).

The transmembrane pressure (d) corresponding to point ($d_1$) on the curve at which point ($d_1$) the curve starts to diverge from the straight line (a), is considered to represent a transmembrane pressure at which fine bubbles which cannot be visually observed begin to form at a pore having a maximum pore diameter.

After the preparation of the graph of FIG. 1, an appropriate value Ph is set so as to satisfy the following formula:

$$d < Ph < c$$

wherein d and c are respectively the transmembrane pressures at points (d) and (c) in FIG. 1.

In step (1) of testing I of the method of the present invention, a first space on one side of the membrane of the module is filled with a liquid chemically inert to said membrane.

As the liquid to be used in testing I, which is chemically inert to the membrane, various liquids can be employed. For example, in the case where the porous polymeric membrane is made of cuprammonium regenerated cellulose, representative examples of such liquids include fluorine-containing liquids, such as a perfluorocarbon liquid and a flon, such as Freon (registered trademark), alcohols, such as ethanol and methanol, and hydrocarbon solvents, such as hexane and pentane.

In the method of the present invention, it is preferred that the liquid to be used in testing I exhibits a surface tension of not greater than about 25 dyne/cm and the gas to be used in testing I exhibits a solubility of about 1.0 $cm^3$-gas/$cm^3$-liquid for the liquid in terms of Ostwald's solubility coefficient.

When a liquid exhibiting a surface tension of not greater than 25 dyne/cm is used in testing I instead of water exhibiting a surface tension as large as about 70 to 75 dyne/cm, which has conventionally been used in the measurement of the capability of a filter for removing bacteria, it becomes possible to conduct testing I at a transmembrane pressure which is not greater than about one-third the transmembrane pressure which is needed when water is used as a liquid in testing I. For example, when a porous polymeric membrane module employing a membrane having a maximum pore diameter of 100 nm is subjected to testing I, by the use of a liquid exhibiting a surface tension of not greater than about 25 dyne/cm, a transmembrane pressure at which formation of visually observable bubbles occurs can be held down to not greater than about 10 kg/$cm^2$, which is one-third the transmembrane pressure (30 kg/$cm^2$) at which formation of visually observable bubbles occurs with the use of water as a liquid.

In step (2) of testing I of the method of the present invention, a second space on the other side of the membrane of the module is supplied with a gas chemically inert to the membrane.

As the gas to be used in testing I, which is chemically inert to the membrane, various gases can be employed. For example, in the case where the porous polymeric membrane is made of cuprammonium regenerated cellulose, representative examples of such gases include air, nitrogen gas, helium gas, argon gas and the like.

In step (3) of testing I of the method of the present invention, the supply of the gas is terminated when the transmembrane pressure on the membrane reaches value Ph, which is preliminarily set, based on FIG. 1, as mentioned above. Then, in step (4), the module is allowed to stand, thereby causing the transmembrane pressure on the membrane to be lowered and, in step (5), a transmembrane pressure lowering from value Ph a predetermined period of time after the termination of the supply of the gas is measured.

The period of time after the termination of the supply of the gas, at which a transmembrane pressure lowering from value Ph is measured (hereinafter frequently referred to as "measuring time") is defined as a period of time at which a first module (defined as the module to be subjected to testing I) exhibits a smaller transmembrane pressure lowering than a second porous polymeric membrane module, said second module being substantially the same as said first module, except that the second module exhibits a lower transmembrane pressure at a point corresponding to point (c) than the first module (module to be subjected to testing I). An example of a method for predetermining the measuring time will be explained below.

At least ten model modules from the model modules constructed in item (3) of the procedure as described above for the preparation of FIG. 1, are individually subjected to first testing comprising the same operations as in steps (1) to (5) of testing I, wherein varied periods of time within 60 seconds are employed as a measuring time for the first testing of each of the model modules. Based on the results of the first testing, periods of time with which a transmembrane pressure lowering can be determined with good reproducibility (which means that the transmembrane pressure lowering values measured at certain periods of time in the first testing do not scatter largely and are within a range defined by $\Delta \bar{P} \pm 0.1 \times \Delta \bar{P}$ wherein $\bar{P}$ represents the average of the transmembrane pressure lowering values measured at the certain periods of time in the first testing) are selected. Then, fresh at least ten model modules from the model modules constructed in item (3) of the procedure as described above for the preparation of FIG. 1, are individually subjected to second testing comprising the same operations as described in item (5) of the above-mentioned procedure for the preparation of FIG. 1 to obtain graphs similar to the graph of FIG. 1, thereby determining points corresponding to point (c) with the respective at least ten model modules. Further, with respect to each model module, the relationships of transmembrane pressure lowering values (corresponding to the above-selected periods of time) to the transmembrane pressures at the points corresponding to point (c) are studied. Among the above-selected periods of time at which transmembrane pressure lowering can be measured with good reproducibility, periods of time at which a first model module exhibits a smaller transmembrane pressure lowering than a second model module which exhibits a lower transmembrane pressure at a point corresponding to point (c) than the first model module, are further selected and can be used as the "measuring time". However, in practice, it is preferred to choose as the measuring time a shortest period of time from the above-further selected periods of time. The reason for the choice of the shortest period of time is that when the measuring time is too long, the ratio of the influence of diffusion of the gas into the liquid at the gas-liquid interface on the transmembrane pressure lowering relative to the influence of the generation of gas bubbles at pores having pore diameters around a maximum pore diameter on the transmembrane pressure lowering, becomes disadvantageously large.

The "measuring time" which is once determined for model modules containing specific porous polymeric membranes, can be commonly used in testing modules as long as not only the production conditions for porous polymeric membranes but also the prescribed ranges of the average pore diameter and maximum pore diameter (corresponding to bubble point pressure) of the membranes are not changed for the modules to be tested.

In the conventional pressure hold test, the supply of a gas is terminated at a transmembrane pressure which is lower than a transmembrane pressure at which fine bubbles that cannot be visually observed begin to form, and then a transmembrane pressure lowering is determined a predetermined period of time after the termination of the supply of the gas. Accordingly, in the conventional pressure hold test, the transmembrane pressure lowering measured is due mainly to the diffusion of the gas, but not formation of bubbles, so that the period of time between the termination of the supply of a gas and the determination of a transmembrane pressure lowering is inevitably long, namely, at least about 10 minutes.

By contrast, in the method of the present invention, the supply of a gas is terminated at a predetermined transmembrane pressure (Ph) which is higher than a transmembrane pressure (d) at which fine bubbles that cannot be visually observed are considered to begin to form, and then a transmembrane pressure lowering from value Ph is determined a predetermined period of time after the termination of the supply of the gas. Accordingly, in the method of the present invention, the transmembrane pressure lowering detected is due mainly to the formation of bubbles, so that the period of time between the termination of the supply of the gas and the determination of a transmembrane pressure lowering can be extremely decreased to, generally 1 to 60 seconds, preferably 5 to 45 seconds.

In another aspect of the present invention, after the evaluation of the virus-removing capability of a porous polymeric membrane module, a module having a desired virus-removing capability is selected by a method comprising the steps of:

(6) determining whether the measured transmembrane pressure lowering is not greater than a value which is predetermined in accordance with a preselected virus removal ratio, and (7) identifying the module as qualified or disqualified, based on said determination in step (6).

In step (6) of the present invention, a determination is made as to whether the measured transmembrane pressure lowering is not greater than a value which is predetermined in accordance with a preselected, desired virus removal ratio. The upper limit value of transmembrane pressure lowering as a criterion for the selection of a porous polymeric membrane module can be determined from the relationship between the virus removal ratio (in terms of logarithmic virus rejection coefficient, $\Phi$) and the transmembrane pressure lowering (as shown in FIG. 3).

In the present invention, the virus removal ratio is expressed in terms of logarithmic virus rejection coefficient $\Phi$ which is defined by the following formula:

$$\Phi = \log(N_o/N_f)$$

wherein $N_o$ is the virus concentration (in terms of $TCID_{50}/ml$, 50% tissue culture infectious dose/ml) of the virus-containing fluid before filtration, and $N_f$ is the virus concentration (in terms of $TCID_{50}/ml$) of the filtrate obtained by the filtration.

In the case of the filtration to remove bacteria by means of a filter for removing bacteria, since bacteria can multiply by itself without a host cell, it is required that no bacteria be present in the filtrate obtained by one time filtration. On the other hand, since a virus cannot multiply by itself without a host cell, in the case of the filtration to remove viruses by means of a porous polymeric membrane module for removing viruses, it is possible to express the virus-removing capability in terms of the ratio of the virus concentration of the virus-containing fluid before filtration to the virus concentration of the filtrate obtained by the filtration (virus removal ratio). Accordingly, in the present invention, the virus-removing capability of the module to remove a virus is expressed in terms of a logarithmic virus rejection coefficient ($\Phi$) value defined above.

In determining a $\Phi$ value of a module, the virus concentration $N_f$ of the filtrate in the above formula is practically determined as follows. After the filtration of a virus-containing fluid, several aliquots of the filtrate are taken and diluted to various concentrations, and individually cultured with an appropriate culture host to thereby infect the host with any unremoved viruses. From each of the ratios of the virus-infected host to the total host, which is obtained with respect to each of the cultured aliquots, the virus concentration (in terms of $TCID_{50}/ml$) of the whole filtrate is determined. When the host is not infected with any of the cultured aliquots of the filtrate, it can be presumed that the whole filtrate contains no virus. In this case, however, for safety, the virus concentration of the whole filtrate is defined as $10^{0.5}$ $TCID_{50}/ml$ when the virus concentration of the virus-containing fluid before filtration is $10^x$ $TCID_{50}/ml$. Accordingly, it is highly possible that the actual $\Phi$ value of such module is higher than $\log(10^x/10^{0.5})$. Further, it is noted that since a virus cannot multiply by itself without a host cell, removal of viruses from a virus-containing liquid by filtration using a module can be performed by multi-step process. Therefore, the required level of virus-removing capability is generally expressed as a certain $\Phi$ value (obtained by the above formula) "or more".

With respect to an example of the actual procedure for predetermining the upper limit of the transmembrane pressure lowering measured at step (5), which upper limit is a criterion for identifying the test module as qualified or disqualified, explanation is made below.

At least 20 model modules from the model modules constructed in item (3) as described above for the preparation of FIG. 1, are individually subjected to third testing comprising the same operations as in steps (1) to (5) in testing I, to thereby measure a transmembrane pressure lowering from value Ph with respect to each module. In this instance, it is preferred that the model modules exhibit a wide variety of transmembrane pressure lowering values, so that such a graph as shown in FIG. 3 is prepared, in which the graph shows the relationship between the transmembrane pressure lowering from value Ph a predetermined period of time after the termination of the supply of a gas in the third testing and the capability to remove a virus in terms of the logarithmic virus rejection coefficient ($\Phi$) for the virus. This procedure is more illustratively described below.

For example, when the virus to be removed is JEV (Japanese encephalitis virus), the size of which is about 45 nm, model porous polymeric membrane modules each containing a porous polymeric membrane having an average pore diameter of $35\pm2.0$ nm and a maximum pore diameter of about 60 to about 80 nm are employed. In addition, in order to disperse the transmembrane pressure lowering values, various types of model modules exhibiting various transmembrane pressure lowering values are prepared by an appropriate method. For example, various model modules are prepared using both a large number of porous hollow fibers each having an average pore diameter of about $35\pm2.0$ nm and a maximum pore diameter of about 60 to about 80 nm and having an effective surface area of 0.03 m$^2$, and a predetermined smaller number of porous polymeric membranes each having a varied average pore diameter of greater than 35 nm, for example, 75 nm. These at least 20 model modules are individually subjected to third testing, to thereby determine a transmembrane pressure lowering from value Ph a predetermined period of time after the termination of the supply of the gas. Further, the capability to remove JEV in terms of the logarithmic virus rejection coefficient ($\Phi$) is determined with respect to each of the model modules. The logarithmic virus rejection coefficient ($\Phi$) of each of the model modules is determined by calculation in the manner mentioned above. Based on the results, a graph as shown in FIG. 3 is prepared.

FIG. 3 is a graph showing the relationship between a transmembrane pressure lowering from value PH a predetermined period of time after the termination of the supply of a gas in the third testing and the capability to remove JEV in terms of the logarithmic virus rejection coefficient ($\Phi$) for JEV, both of which are determined with respect to each of at least 20 model modules each containing a porous polymeric membrane having an average pore diameter of $35\pm2.0$ nm and a maximum pore diameter of about 60 to about 80 nm and having an effective surface area of 0.03 m$^2$, wherein the at least 20 model modules comprise those not containing and those containing hollow fibers having varied average pore diameters. In FIG. 3, a filled circle having an arrow directed upward indicates that the $\Phi$ value represented by the filled circle is a value such that an actual $\Phi$ value corresponding to the filled circle may be higher than that as indicated.

In the experiment conducted to prepare the graph of FIG. 3, a perfluorocarbon liquid having a surface tension of 15.0 dyne/cm and nitrogen gas having a solubility of 0.37 cm$^3$-gas/cm$^3$-liquid for perfluorocarbon liquid in terms of Ostwald's solubility coefficient were used as a liquid and a gas in the third testing and the measuring time was 15 seconds.

FIG. 3 indicates that in order to attain a $\Phi$ value of at least 4.5, the upper limit of the transmembrane pressure lowering is 2.5 atm. Practically, a $\Phi$ value is arbitrarily set according to the objective of the use of a porous polymeric membrane module for removing a virus.

Another example in which the upper limit of a transmembrane pressure lowering value is determined with respect to AIDS virus, is explained below, taking as an example the case wherein a perfluorocarbon liquid having a surface tension of 15.0 dyne/cm and nitrogen gas having a solubility of 0.37 cm$^3$-gas/cm$^3$-liquid for perfluorocarbon liquid in terms of Ostwald's solubility coefficient are used as a liquid and a gas in the third testing.

When the virus to be removed is HIV (human immunodeficiency virus, i.e., AIDS virus), the size of which is about 100 nm, a model porous polymeric membrane module containing a porous polymeric membrane having, for example, an average pore diameter of $75\pm4.0$ nm and a maximum pore diameter of about 120 to about 175 nm and having an effective surface area of 0.01 m$^2$ is employed. Value Ph is set at a transmembrane pressure of 4.0 kg/cm$^2$ and the measuring time is set at 15 seconds Substantially the same procedure as mentioned above in connection with the preparation of the graph of FIG. 3 is conducted, except that the conditions are changed accordingly, thereby obtaining a graph showing the relationship between a transmembrane pressure lowering from value Ph a predetermined period of time (15 seconds) after the termination of the supply of a gas in the third testing and the capability to remove HIV in terms of the logarithmic virus rejection coefficient ($\Phi$) for HIV. As a result, it is found that in order to attain a logarithmic rejection coefficient $\Phi$ of at least 5.0, the transmembrane pressure lowering from value Ph 15 seconds after the termination of the supply of the gas should be not greater than 1.5 kg/cm$^2$.

After determining whether the measured transmembrane pressure lowering is not greater than a value which is predetermined in accordance with a preselected virus removal ratio [step(6)], and the module is identified as qualified or disqualified, based on the above determination [step(7)].

Figure 2:
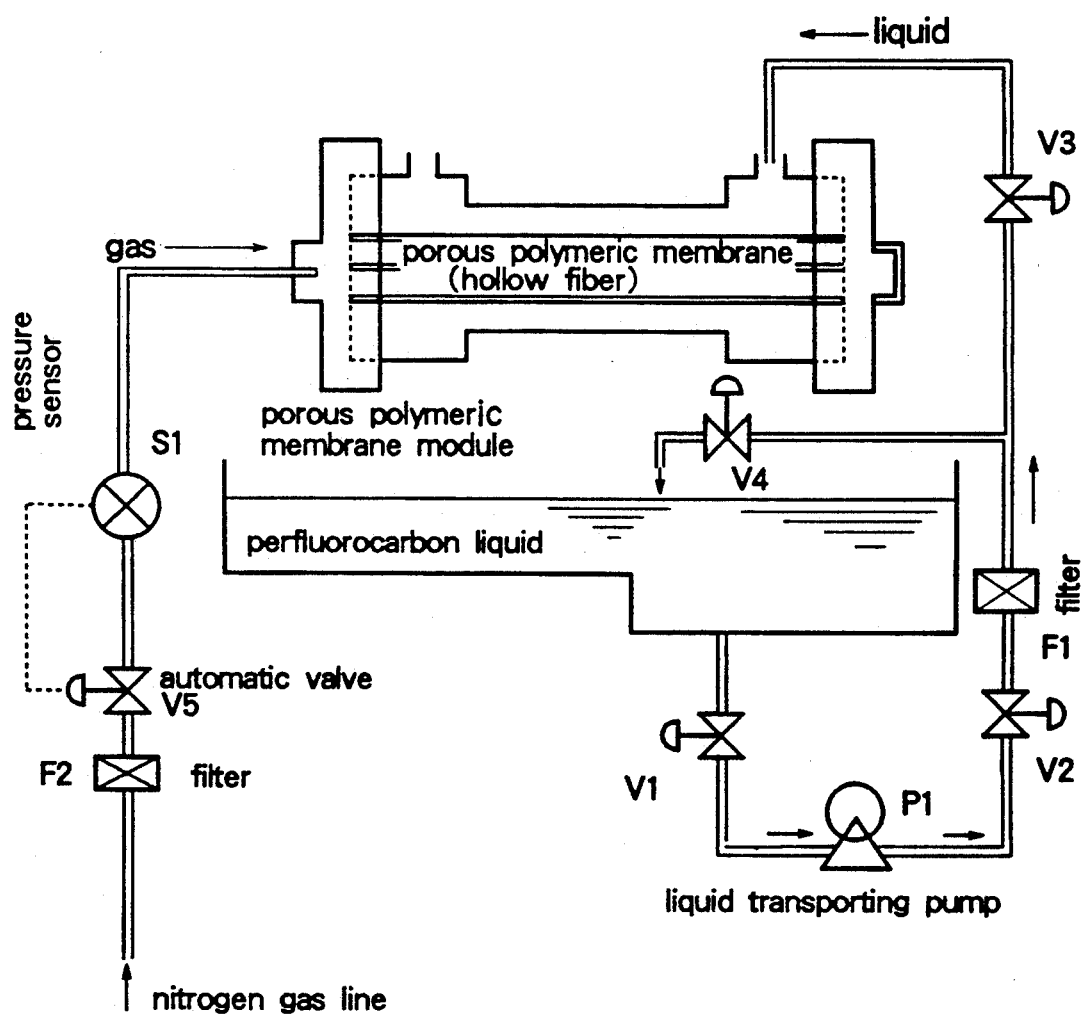
FIG. 2 is a diagram illustrating a preferred embodiment of apparatus employed according to the method of the present invention.

Referring now to FIG. 2, the method of the present invention will now be illustrated as follows.

In FIG. 2, there is shown a diagram illustrating a preferred embodiment of the method of the present invention.

First, a vessel for liquid is filled with a perfluorocarbon liquid exhibiting a surface tension of 15.0 dyne/cm, and a porous polymeric membrane module to be examined is provided. The module comprises a casing having an inlet for a virus-containing fluid and an outlet for a filtrate, and a porous polymeric membrane (hollow fiber membrane) disposed in the casing to partition the interior of the casing into a first space on one side of the membrane which first space communicates with one of the inlet or outlet and a second space on the other side of the membrane which second space communicates with the remaining one of the inlet or outlet.

Then, valves V1, V2 and V3 are opened and valve V4 is closed. The perfluorocarbon liquid is transported by liquid transporting pump P1 through valve V1, pump P1, valve V2, filter F1 and valve V3, and injected into the first space on one side of the membrane, to thereby fill the first space with the perfluorocarbon liquid.

Then, automatic valve V5 is opened to supply the second space on the other side of the membrane with nitrogen gas exhibiting a solubility of 0.37 $cm^3$-gas/$cm^3$-liquid for the perfluorocarbon liquid in terms of Ostwald's solubility coefficient, from nitrogen gas line through filter F2, automatic valve V5 and pressure sensor S1 while detecting the transmembrane pressure by pressure sensor S1. When the transmembrane pressure on the membrane monitored by sensor S1 has reached a predetermined value Ph, the supply of the nitrogen gas is terminated by automatic valve V5.

The module is allowed to stand, thereby causing the transmembrane pressure on the membrane to be lowered. A transmembrane pressure lowering from value Ph a predetermined period of time after the termination of the supply of the gas is measured.

Determination is made as to whether the transmembrane pressure lowering value thus measured is not greater than a value which is predetermined according to a preselected virus-removing capability, i.e., logarithmic virus rejection coefficient $\Phi$. When the transmembrane pressure lowering value is equal to or smaller than the predetermined value, the tested module is selected as an acceptable (qualified) module. When the transmembrane pressure lowering value is greater than the predetermined value, the tested module is excluded as an unacceptable (disqualified) module.

As described above, according to the method of the present invention, if a desired average pore diameter of a porous polymeric membrane, Ph value and "measuring time" are once determined in accordance with the type of a virus to be removed and with the desired level of virus-removing capability in terms of a $\Phi$ value, the virus-removing capability of a porous polymeric membrane module can be evaluated according to steps (1) to (5) of the method of the present invention. And if the upper limit of the transmembrane pressure lowering at the "measuring time" (for a module to be identified as qualified) is determined in accordance with the desired $\Phi$ value, the module having a desired level of $\Phi$ can be easily selected according to steps (6) to (7) following steps (1) to (5) of the method of the present invention.

For practicing the evaluation of and the selection of the module more effectively and more efficiently by the method of the present invention, it is desired that the modules to be evaluated and selected have porous polymeric membranes having an average pore diameter and a maximum pore diameter within predetermined ranges. From this view point, it is preferred that the modules to be tested are those which have been produced using porous polymeric membranes preselected, for example in accordance with production batches, so that the membranes have an average pore diameter and a maximum pore diameter which are, respectively, within predetermined ranges.

Meanwhile, in the field of filters for removing bacteria, manufacturers of bacteria-removing filters have developed methods for examining the capability of a bacteria-removing filter to remove bacteria. In this field, it has recently been desired for manufacturers to provide users of bacteria-removing filters with methods for examining the capability of bacteria-removing filters, so that users themselves can check the bacteria-removing capability of such filters before and/or after the use thereof. Recently, also in the field of modules for removing a virus, due to the fact that the development and use of modules for removing a virus are growing, it is becoming desirable to provide a double testing system in which a testing of a module by the manufacturer is effectively combined with testing of the module by the user of the module so that the user can check whether or not a predetermined level of the capability to remove the virus has been maintained after the testing by the manufacturer.

Accordingly, in the present invention, it is preferred that the method of the present invention further comprise, after testing I, a non-destructive or destructive testing with respect to the maintenance of a predetermined level of the capability to remove the virus.

When a porous polymeric membrane module has been selected by conducting testing I described above, it is sure that the tested module has a predetermined level of the capability to remove a virus at least at the time of testing I. Therefore, when, after testing I, the module has suffered no damage, especially in the porous polymeric membrane disposed therein, the predetermined level of the capability to remove a virus is surely exhibited by the module. However, if it is possible that, after testing I, the module has suffered any damage, especially in the membrane disposed therein, it is desired to confirm, before and/or after the use thereof, that the predetermined level of the virus-removing capability is maintained.

As described above, since testing I is to be conducted on a module before use, it is necessary that testing I of the method of the present invention be a non-destructive testing.

On the other hand, the further testing (testing II) which may be conducted after testing I may be either non-destructive or destructive, depending on whether the further testing is to be conducted before or after the use of the module. When the further testing is to be conducted before the use of the module, it is requisite that the further testing be nondestructive. However, when the further testing is to be conducted on samples of modules, the further testing may be destructive even when conducted before use.

With respect to the further testing (testing II), it should be noted that since a module which is to be subjected to testing II has necessarily already been subjected to testing I, so that it has already been completely confirmed that the module has the predetermined level of the virus-removing capability, testing II may be a relatively simple testing as long as it can be effectively confirmed that after testing I, the module has not suffered damage due to strong impacts, drastic temperature changes, extremely high pressures, etc. which might have been caused during the storage or use. Thus, with respect to testing II, it is not needed to conduct strict measurement of, e.g., the maximum pore diameter and average pore diameter of the porous polymeric membrane used in the module.

Accordingly, a more preferred mode of the method of the present invention further comprises, after testing I, subjecting the module to non-destructive testing (testing II) including filling the first space of the module with water and applying a transmembrane pressure of up to about 2.0 kg/cm² to the membrane by supplying a gas to the second space of the module, and determining whether generation of visually observable bubbles does not occur in the first space filled with the water.

In this instance, if bubbles are generated at such an extremely low transmembrane pressure, it is apparent that the membrane used in the module has suffered serious damage, such as a break, and thus, the module cannot suitably be used for removing a virus. In this connection, it should be noted that a porous polymeric membrane for removing viruses, which generally has a particle size of not larger than about 300 nm, has extremely fine pores suitable for removing viruses and that it is impossible for a module having a complete pore structure without any defect in the membrane to generate a bubble at a transmembrane pressure as low as up to about 2.0 kg/cm².

Examples of gases usable in this testing II to be conducted in the more preferred mode of the method of the present invention include the same gases as mentioned above in connection with testing I.

The above-mentioned testing II in which examination is conducted with respect to the generation of bubbles at a transmembrane pressure of up to about 2.0 kg/cm² is hereinafter frequently referred to as the "leak test." By the "leak test", it can be determined in a simple manner whether or not the membrane has suffered any damage, such as great expansion of pores and occurrence of breaks.

However, if it is desired to more strictly confirm the maintenance of a predetermined level of the virus-removing capability of a module after testing I, testing II may be conducted in a different manner.

Accordingly, another more preferred mode of the method of the present invention further comprises, after testing I, non-destructive testing (testing II) including filling the first space with water, applying a transmembrane pressure of up to about 2.0 kg/cm² to the membrane by supplying a gas to the second space, terminating the supply of the gas, allowing the module to stand, thereby causing the transmembrane pressure on the membrane to be lowered, and determining whether a transmembrane pressure lowering from the applied pressure does not occur before about 10 minutes after the termination of the supply of the gas.

In this more preferred mode of the method of the present invention, by this testing II after testing I, whether or not the membrane has suffered relatively minor damage which may not be detected by the above-mentioned leak test, suitably can be confirmed by determining any lowering of transmembrane pressure due to the increased dispersion of the gas into the water.

When a transmembrane pressure as low as up to about 2.0 kg/cm² is applied to the membrane of a module which has suffered no damage after testing I, it is not possible for the normal membrane to exhibit any transmembrane pressure lowering. Therefore, if any transmembrane pressure lowering is detected after the application of a transmembrane pressure as low as up to about 2.0 kg/cm², it is apparent that the module has suffered some damage in the membrane after testing I, so that the module cannot suitably be used for removing a virus from a virus-containing fluid.

Examples of gases, usable in this testing II to be conducted in this more preferred mode of the method of the present invention, include the same gases as mentioned above in connection with testing I.

In the above-mentioned two more preferred modes of the method of the present invention, non-destructive testing (testing II) is conducted after testing I. However, if it is desired to further confirm the maintenance of the predetermined level of the virus-removing capability of the module, destructive testing may be conducted as testing II after testing I.

Accordingly, still another preferred mode of the method of the present invention further comprises, after testing I, subjecting the module to destructive testing (testing II) including applying to the module a fluid containing a virus substitute to be separated by filtration, and determining whether the module is capable of removing the substitute at least at a preselected removal ratio.

Representative examples of fluids containing a virus substitute include an aqueous solution or dispersion of the virus substitute.

With respect to the virus substitute, there is no particular restriction as long as it has a particle diameter which is about the same as that of the virus which is to be removed by the module, and it has a narrow particle diameter distribution.

Representative examples of virus substitutes include colloidal gold particles and fine particles of polystyrene latex.

The method for evaluating the virus-removing capability of a module by using a virus substitute is more illustratively described as follows.

For the evaluation of the virus-removing capability of a module by using a virus substitute, a module having a predetermined level of the virus-removing capability is provided and a fluid containing a virus substitute is applied to the module and a logarithmic rejection coefficient ($\Phi$) is determined for the virus substitute. This logarithmic rejection coefficient ($\Phi$) for the substitute is used as a standard for evaluating the virus-removing capability of a module. This procedure is further described below, taking as an example the case in which colloidal gold particles are used as a substitute for Japanese encephalitis virus (JEV).

As mentioned above, when a module employing a porous polymeric membrane having an average pore diameter of 35±2.0 nm and a maximum pore diameter of about 60 nm to about 80 nm and having an effective surface area of 0.03 m² exhibits a transmembrane pressure lowering of 2.5 kg/cm² or less as determined by testing I described above, it has a JEV-removing capability represented by a $\Phi$ value of 4.5 or more. When the present inventors conducted experiments in which an aqueous dispersion of colloidal gold particles having an average particle diameter of 40 nm was applied to a plurality of such modules, all modules exhibited a logarithmic rejection coefficient for colloidal gold particles ($\Phi_g$) of 2.5 or more. The results of the experiments show that when the above-mentioned modules (which employ a porous polymeric membrane having an diameter of 35±2.0 nm and a maximum pore diameter of about 60 to about 80 nm and having an effective surface area of 0.03 m² and which exhibit a transmembrane pressure lowering of 2.5 kg/cm² or less as determined by testing I) exhibit a logarithmic rejection coefficient ($\Phi_g$) of 2.5 or more for colloidal gold particles having an average particle diameter of 40 nm, it can be concluded that the predetermined level of the JEV-removing capability thereof, i.e., a logarithmic virus rejection coefficient (Φ) of 4.5 or more has been maintained after testing I.

In the present invention, in addition to testing I, the above-mentioned destructive and non-destructing testings (testing II) can be employed individually or in combination.

In still another aspect of the present invention, there is provided a method for removing viruses from a virus-containing fluid, which comprises subjecting a virus-containing fluid to filtration through the porous polymeric membrane module evaluated by steps (1) to (5) and selected by steps (6) to (7) following steps (1) to (5) of the method of the present invention.

Although the above description is made with respect to a porous polymeric membrane module for removing viruses, it will be well understood that the method of the present invention can also be applied to a porous polymeric membrane module for removing other microorganisms which, like a virus, need a host cell for multiplication thereof. Examples of such microorganisms include Rickettsia, Chlamydia and the like.

PREFERRED EMBODIMENT OF THE INVENTION

The present invention will now be described in more detail with reference to the following Examples, which should not be construed as limiting the scope of the present invention.

EXAMPLES 1 To 10

Porous hollow fiber polymeric membranes prepared for removing JEV virus and made of cuprammonium regenerated cellulose were provided each having an average pore diameter of 35.0±2.0 nm as measured based on water permeability and having a bubble point value of 9.5±0.5 kg/cm² (corresponding to a maximum pore diameter of about 60 to about 80 nm) as measured by using perfluorocarbon liquid having a surface tension of 15.0 dyne/cm and nitrogen gas. Using these porous hollow fiber polymeric membranes, 10 porous polymeric membrane modules each having an effective surface area of 0.03 m² were produced. Each module comprised a casing having an inlet for a virus-containing fluid and an outlet for a filtrate, and a porous polymeric membrane disposed in the casing to partition the interior of the casing into a first space on one side of the membrane which first space communicated with the outlet and a second space on the other side of the membrane which second space communicated with the inlet.

The 10 modules were individually subjected to the following testing: The first space on one side of the membrane was filled with perfluorocarbon liquid having a surface tension of 15.0 dyne/cm [step (1)]. The second space on the other side of the membrane was supplied with nitrogen gas [step (2)]. The supply of the gas was terminated when the transmembrane pressure on the membrane reached a predetermined value Ph of 8.0 kg/cm² [step(3)], the 1 value Ph satisfying the following formula:

$$d < Ph < c$$

wherein d and c are respectively the transmembrane pressures at points (d) and (c) in a graph as shown in FIG. 1 obtained with respect to a model module containing a porous polymeric membrane having an average pore diameter and a maximum pore diameter which are, respectively, about 35±2.0 nm and about 60 to about 80 nm. The transmembrane pressures of d and c are, respectively, 6.0 kg/cm² and 9.5 kg/cm².

The module was allowed to stand, thereby causing the transmembrane pressure on the membrane to be lowered step (4)], and a transmembrane pressure lowering from value Ph 15 seconds (which was obtained, based on the average pore diameter of 35 nm ±2.0 nm and a maximum pore diameter of about 60 to about 80 nm, by the method described herein) after the termination of the supply of the gas was measured [step (5)]. The results are shown in Table 1.

As shown in Table 1, with respect to 8 modules (module Nos. 1 to 8) of the 10 modules, the transmembrane pressure lowering was smaller than 2.5 kg/cm² which was the previously determined upper limit of a transmembrane pressure lowering value which is capable of attaining a logarithmic virus rejection coefficient (Φ) of 4.5 or more (the relationship between the upper limit of the transmembrane pressure lowering and the logarithmic virus rejection coefficient Φ was obtained by preparing a graph as shown in FIG. 3 by the method described herein). One module (module No. 9) exhibited a transmembrane pressure lowering value which was greater than the upper limit value 2.5 kg/cm².The other module (module No. 10) exhibited a drastic bubbling at several portions of the porous hollow fiber membrane, so that the transmembrane pressure was not be able to be raised to value Ph of 8.0 kg/cm² and the maximum transmembrane pressure was lower than 6 kg/cm². Occurrence of drastic bubbling at such a low transmembrane pressure indicates that the porous hollow fiber membrane is defective.

Thus, the 8 modules (module Nos. 1 to 8), each of which had exhibited a transmembrane pressure lowering value smaller than 2.5 kg/cm², were selected. Each of the selected modules was filled with water and subjected to high-pressure steam sterilization at 121° C. for 30 minutes.

Then, before being used for removing JEV virus, each module was subjected to a "leak test" (testing II) at a transmembrane pressure of 1.0 kg/cm² using nitrogen gas. As a result, each module exhibited no visible generation of bubbles, indicating that the capability to remove JEV virus had been maintained.

Thereafter, each module was subjected to virus removing testing employing Japanese encephalitis virus (JEV), which has a diameter of about 45 nm. As a virus-containing fluid, use was made of a minimum essential medium containing fetal calf serum and having a JEV concentration of $10^{5.8} TCID_{50}/$ ml. As a result, as shown in Table 1, each module exhibited an excellent virus removing capability represented by a Φ value of 5.0 or more.

After the virus removing testing, each module was rinsed with an aqueous solution containing 0.1 % (w/v) of NaOH and 0.1 % (w/v) of surfactants. Then, in order to confirm the capability to remove JEV virus, module Nos. 1, 3, 5 and 7 were subjected to a test (testing II) wherein an aqueous dispersion of colloidal gold particles having an average diameter of 40 nm which were a substitute for JEV virus (colloidal gold concentration: $7.76 \times 10^{10}$/ml) was applied to each module, to thereby examine the capability of each module to remove the substitute. At the same time, module Nos. 2, 4, 6 and 8 were subjected to the same "leak test" (testing II) as mentioned above.

As a result, as shown in Table 1, each of module Nos. 1, 3, 5 and 7 exhibited a logarithmic colloidal gold rejection coefficient ($\Phi_g$) of 3.2 or more, which is well higher than 2.5 which is the lower limit of $\Phi_g$ corresponding to a logarithmic virus rejection coefficient ($\Phi$) of 4.5 or more. Further, with respect to the "leak test" (testing II) of modules Nos. 2, 4, 6 and 8, no generation of visible bubbles was observed. Thus, it was found that modules Nos. 1 to 8 had suffered no damage before or during the use thereof for removing the virus.

The two modules (module Nos. 9 and 10) which had been excluded as unacceptable modules were filled with water and subjected to high-pressure steam sterilization in the same manner as mentioned above. Then, the two modules were subjected to a "leak test" (testing II) at a transmembrane pressure of 1.0 kg/cm² in the same manner as mentioned above. As a result, in the case of module No. 9, the generation of bubbles was visually observed at a portion of the follow fiber membrane at a transmembrane pressure as low as 0.9 kg/cm², indicating the presence of an unacceptably large pore or break. In the case of module No. 10, no generation of bubbles was observed in the "leak test".

Then, the two modules were subjected to virus removing testing employing Japanese encephalitis virus in the same manner as mentioned above. As a result, module Nos. 9 and 10 exhibited $\Phi$ values as low as 2.6 and 0.5 respectively, which are lower than the desired range of 4.5 or more. In the case of module No. 10, most of the virus particles passed through the hollow fiber membrane without being trapped.

Further, module No. 9 was washed with a rinsing solution of the same type as mentioned above and then, subjected to colloidal-gold removing testing (testing II) using, as a substitute for virus, colloidal gold particles (average particle diameter: 40 nm) in the same manner as mentioned above. As a result, the $\Phi_g$ value was as low as 1.2.

space communicates with the remaining one of said inlet or outlet, which method comprises subjecting said porous polymeric membrane module to testing I, said testing I comprising the steps of:
(1) filling the first space on one side of said membrane with a liquid, chemically inert to said membrane,
(2) supplying the second space on the other side of said membrane with a gas, chemically inert to said membrane,
(3) terminating the supply of said gas when the transmembrane pressure on said membrane reaches predetermined value Ph, said value Ph satisfying the following formula:

$$d < Ph < c$$

wherein d and c are respectively the transmembrane pressures at points (d) and (c) in FIG. 1 hereof,
(4) allowing the module to stand, thereby causing the transmembrane pressure on said membrane to be lowered, and
(5) measuring the transmembrane pressure lowering from value Ph a predetermined period of time after the termination of the supply of the gas, wherein FIG. 1 is a graph containing a curve showing the relationship between the transmembrane pressure and the gas supply rate of a model porous polymeric membrane module, said model module being substantially the same as said module to be subjected to testing I, containing a porous polymeric membrane having an average pore diameter and a maximum pore diameter which are, respectively, within ranges which are predetermined in accordance with the size of viruses to be removed, said relationship between the transmembrane pressure and the gas supply rate being obtained by filling the first space on one side of the membrane of said model module with a liquid chemically inert to the membrane and supplying the second space on the other

TABLE 1

| Example No. | 1 | 2 | 3 | 4 | 5 | 6 | 7 | 8 | 9 | 10 |
|---|---|---|---|---|---|---|---|---|---|---|
| Module No. | No. 1 | No. 2 | No. 3 | No. 4 | No. 5 | No. 6 | No. 7 | No. 8 | No. 9 | No. 10 |
| Hollow fiber | | | | | | | | | | |
| Average pore diameter (nm) | 35.2 | 35.2 | 36.5 | 36.5 | 34.0 | 34.0 | 34.5 | 34.5 | 35.2 | 34.0 |
| Bubble point | 9.6 | 9.6 | 9.3 | 9.3 | 9.5 | 9.5 | 9.8 | 9.8 | 9.6 | 9.5 |
| Effective surface area (m²) | 0.03 | 0.03 | 0.03 | 0.03 | 0.03 | 0.03 | 0.03 | 0.03 | 0.03 | 0.03 |
| Transmembrane pressure lowering (kg/cm²) | 1.9 | 2.1 | 2.2 | 2.3 | 1.7 | 1.9 | 1.6 | 1.8 | 3.1 | —* |
| Leak test (before use) | No bubbles | No bubbles | No bubbles | No bubbles | No bubbles | No bubbles | No bubbles | No bubbles | No bubbles | Bubbles were generated |
| $\Phi$(JEV) | ≧5.3 | ≧5.3 | 5.1 | 5.0 | ≧5.3 | ≧5.3 | ≧5.3 | ≧5.3 | 2.6 | 0.5 |
| $\Phi_g$ (colloidal gold) | 3.7 | — | 3.2 | — | ≧4.0 | — | ≧4.0 | — | 1.2 | — |
| Leak test (after use) | — | No bubbles | — | No bubbles | — | No bubbles | — | No bubbles | — | — |

Note*: Transmembrane pressure could not be sufficiently raised to measure lowering thereof.

What is claimed is:

1. A method for evaluating the virus-removing capability of a porous polymeric membrane module for removing viruses from a virus-containing fluid by filtration, said module comprising a casing having an inlet for a virus-containing fluid and an outlet for a filtrate, and a porous polymeric membrane disposed in said casing to partition the interior of said casing into a space communicates with one of said inlet or said outlet and a second space on the other side of said membrane which second side of the membrane of said model module with a gas chemically inert to the membrane while measuring the transmembrane pressure and the gas supply rate, and wherein:

a straight line obtained by extending the straight line portion first occurring in the curve of FIG. 1 is defined as straight line (a), said first occurring straight line portion of the curve representing the increase in gas supply rate in proportion to the increase in transmembrane pressure, a transmembrane pressure at point (d) corresponding to point ($d_1$) on the curve at which point ($d_1$) said curve starts to diverge from said straight line (a), is defined as transmembrane pressure d, a straight line obtained by connecting points (e) and (f) on the curve at which points (e) and (f) the gas supply rates are, respectively, 2.5 times and 3.0 times the gas supply rate at point ($d_1$), is defined as straight line (b), and a transmembrane pressure at point (c) corresponding to point ($c_1$) at which straight line (a) intersects with straight line (b), is defined as transmembrane pressure c.

2. The method according to claim 1, wherein said liquid to be used in testing I exhibits a surface tension of not greater than 25 dyne/cm and said gas to be used in testing I exhibits a solubility of not greater than 1.0 $cm^3$-gas/$cm^3$-liquid for said liquid in terms of Ostwald's solubility coefficient.

3. The method according to claim 1, wherein said predetermined period of time after the termination of the supply of the gas in step (5) is a period of time at which a first module defined as said module to be subjected to testing I exhibits a smaller transmembrane pressure lowering than a second porous polymeric membrane module, said second module being substantially the same as said first module, except that said second module exhibits a lower transmembrane pressure at a point corresponding to point (c) than said first module.

4. The method according to claim 1, further comprising, after testing I, subjecting the tested module to testing II selected from non-destructive testing and destructive testing, to thereby determine whether the evaluated virus-removing capability of said module is maintained.

5. The method according to claim 4, wherein said non-destructive testing includes filling said first space of the module with water and applying a transmembrane pressure of up to about 2.0 kg/$cm^2$ to said membrane by supplying a gas to said second space of the module, and determining whether generation of visually observable bubbles does not occur in said first space filled with the water.

6. The method according to claim 4, wherein said non-destructive testing includes filling said first space with water, applying a transmembrane pressure of up to about 2.0 kg/$cm^2$ to said membrane by supplying a gas to said second space, terminating the supply of the gas, allowing the module to stand, thereby causing the transmembrane pressure on said membrane to be lowered, and determining whether a transmembrane pressure lowering from the applied pressure does not occur before about 10 minutes from the termination of the supply of the gas.

7. The method according to claim 4, wherein said destructive testing includes applying to said module a fluid containing a substitute for the viruses to be removed by filtration, to thereby evaluate the capability of said module to remove said substitute.

8. The method according to any one of claims 1 to 7, wherein said porous polymeric membrane is a porous hollow fiber polymeric membrane.

9. The method according to any one of claims 1 to 7, wherein said porous polymeric membrane is made of cuprammonium regenerated cellulose.

* * * * *

UNITED STATES PATENT AND TRADEMARK OFFICE
CERTIFICATE OF CORRECTION

PATENT NO. : 5,185,082

DATED : February 9, 1993

INVENTOR(S) : Nakano et al.

It is certified that error appears in the above-identified patent and that said Letters Patent is hereby corrected as shown below:

Claim 1, column 21, line 66, after "a" insert --first space on one side of said membrane which first--.

Abstract, line 13, "efficiency" should read --efficiently--.

Signed and Sealed this

Ninth Day of November, 1993

Attest:

BRUCE LEHMAN

Attesting Officer     Commissioner of Patents and Trademarks